US009719963B2

(12) United States Patent
Wu et al.

(10) Patent No.: US 9,719,963 B2
(45) Date of Patent: *Aug. 1, 2017

(54) HIGH PERFORMANCE ION MOBILITY SPECTROMETER APPARATUS AND METHODS

(71) Applicants: Ching Wu, Boxborough, MA (US); Clinton Alawn Krueger, Milton, MA (US); Anthony Joseph Midey, Maynard, MA (US); Mark A Osgood, Brookline, NH (US)

(72) Inventors: Ching Wu, Boxborough, MA (US); Clinton Alawn Krueger, Milton, MA (US); Anthony Joseph Midey, Maynard, MA (US); Mark A Osgood, Brookline, NH (US)

(73) Assignee: Excellims Corporation, Acton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/537,863

(22) Filed: Nov. 10, 2014

(65) Prior Publication Data

US 2015/0069227 A1   Mar. 12, 2015

Related U.S. Application Data

(60) Continuation of application No. 13/475,993, filed on May 20, 2012, now Pat. No. 8,884,221, and a continuation-in-part of application No. 13/360,758, filed on Jan. 29, 2012, now Pat. No. 8,492,712, which is a division of application No. 12/471,101, filed on May 22, 2009, now Pat. No. 8,106,352, which is a continuation of application No. 11/618,430, filed on Dec. 29, 2006, now Pat. No. 7,576,321, said application No. 13/475,993 is a continuation-in-part of application No. 13/360,760, filed on Jan. 29, 2012, now Pat. No. 8,492,708, and a continuation-in-part of application No. 12/695,111, filed on Jan. 27, 2010, now Pat. No. 8,242,442, and a continuation-in-part of application No. 12/577,062, filed on Oct. 9, 2009, now Pat. No. 8,217,338, said application No. 13/475,993 is a continuation-in-part of application (Continued)

(51) Int. Cl.
*G01N 27/62* (2006.01)

(52) U.S. Cl.
CPC ................... *G01N 27/622* (2013.01)

(58) Field of Classification Search
CPC ...................................... G01N 27/622
See application file for complete search history.

(56) References Cited

PUBLICATIONS

Laser Desorption/Ionization of Ultrafine Aerosol Particles Peter G. Carson1, Murray V. Johnston1 and Anthony S. Wexler2 Rapid Communications in Mass Spectrometry, vol. 11, 993-996 (1997).*

(Continued)

*Primary Examiner* — Nicole Ippolito
*Assistant Examiner* — Sean Luck (57) ABSTRACT

An ion mobility spectrometry method wherein ions are separated along a drift axis while providing a drift gas flow in a direction that is substantially neither in the direction of the drift axis nor opposite to the drift axis. Ion mobility spectrometer operation methods use a cross-directional gas flow in a drift tube and/or a segmented drift tube for pre-separation.

7 Claims, 10 Drawing Sheets

Related U.S. Application Data

No. 11/776,392, filed on Jul. 11, 2007, now abandoned.

(60) Provisional application No. 61/488,438, filed on May 20, 2011, provisional application No. 61/104,319, filed on Oct. 10, 2008, provisional application No. 60/891,532, filed on Feb. 26, 2007, provisional application No. 60/807,031, filed on Jul. 11, 2006.

(56) References Cited

PUBLICATIONS

Observation of Aerosol Formation During Laser Ablation Using a Low-Pressure Differential Mobility Analyzer Renato P. Camata, Makoto Hirasawa, Kikuo Okuyamat, and Kazuo Takeuchi J. Aerosol Sci. Yol. 31, No. 4, pp. 391-401, 2000.*

* cited by examiner

HIGH PERFORMANCE ION MOBILITY SPECTROMETER APPARATUS AND METHODS

CROSS-REFERENCE TO RELATED APPLICATIONS

This is a continuation of U.S. patent application Ser. No. 13/475,993, filed May 20, 2012. Application Ser. No. 13/475,993 is a continuation-in-part of U.S. patent application Ser. No. 13/360,758, filed Jan. 29, 2012 and now issued as U.S. Pat. No. 8,492,712, which is a division of application Ser. No. 12/471,101, filed May 22, 2009, the latter now issued as U.S. Pat. No. 8,106,352, which is a continuation of U.S. patent application Ser. No. 11/618,430, filed Dec. 29, 2006, the latter now issued as U.S. Pat. No. 7,576,321, which claims priority from Provisional Application 60/766,226, filed Jan. 2, 2006. Application Ser. No. 13/475,993 is a continuation-in-part of U.S. patent application Ser. No. 13/360,760, filed Jan. 29, 2012, which is a division of application Ser. No. 12/471,101, filed May 22, 2009, the latter now issued as U.S. Pat. No. 8,106,352, which is a continuation of U.S. patent application Ser. No. 11/618,430, filed Dec. 29, 2006, the latter now issued as U.S. Pat. No. 7,576,321, which claims priority from Provisional Application 60/766,226, filed Jan. 2, 2006. Application Ser. No. 13/475,993 is a continuation-in-part of U.S. patent application Ser. No. 12/695,111, filed Jan. 27, 2010. Application Ser. No. 13/475,993 is a continuation-in-part of U.S. patent application Ser. No. 12/577,062, filed Oct. 9, 2009, which claims priority from Provisional Application 61/104,319, filed Oct. 10, 2008. Application Ser. No. 13/475,993 is a continuation-in-part of U.S. patent application Ser. No. 11/776,392, filed Jul. 11, 2007, which claims priority from Provisional Application 60/891,532, filed Feb. 26, 2007 and claims priority from Provisional Application 60/807,031, filed Jul. 11, 2006. Application Ser. No. 13/475,993 also claims the benefit of and priority to corresponding U.S. Provisional Patent Application No. 61/488,438, filed May 20, 2011. The entire contents of all of the above applications are incorporated herein by reference in their entirety.

BACKGROUND OF THE INVENTION

Since it was invented in the early 1970's, ion mobility spectrometry (IMS) has been developed into a powerful analytical tool used in a variety of applications. There are three major forms of this instrument including independent chemical detection systems, chromatographic detectors, or hyphenated IMS mass spectrometry (MS) systems. As an independent detection system, IMS qualitatively and quantitatively detects substances in different forms relying on its capability to ionize the target substance, to separate the target substance from background based on interactions with a drift gas (i.e. a carrier gas), and to detect the substance in its ionized form. As a chromatographic detector, IMS acquires multiple ion mobility spectra of chromatographically separated substances. In combined IMS-MS systems, IMS is used as a separation method to isolate target substances before mass analysis. However, the resolution of IMS is generally consider low, often regulating such devices to qualitative use or use in environments with low levels of interferants with respect to the substances of interest.

The basic common components of an IMS system consist of an ionization source, a drift tube that includes a reaction region, an ion shutter grid, a drift region, and an ion detector. In gas phase analysis the sample to be analyzed is introduced into the reaction region by an inert carrier gas, ionization of the sample is often completed by passing the sample through a reaction region and/or a radioactive 63Ni source. The ions that are formed are directed toward the drift region by an electric field applied to drift rings that establish the drift region, and a narrow pulse of ions is then injected into, and/or allowed to enter, the drift region via an ion shutter grid. Once in the drift region, ions of the sample are separated based upon their ion mobilities and there arrival time at a detector is an indication of ion mobility which can be related to ion mass. However, it is to be understood that ion mobility is not only related to ion mass, but rather is fundamentally related to the ion-drift gas interaction potential which is not solely dependent on ion mass.

Ion mobility spectrometers (IMS) have become a common tool for detecting trace amounts of chemical and/or biological molecules. Compared to other spectrometric chemical analysis technologies, e.g., mass spectrometry, IMS is a relatively low resolution technique. The IMS advantages of very high sensitivity, small size, low power consumption, and ambient pressure operation are in some cases completely offset, or at a minimum, reduced by the lack of sufficient resolution to prevent unwanted responses to interfering chemical and/or biological molecules. The false positives that result can range from minor nuisances in some scenarios to major headaches in others. Interfering chemical and/or biological molecules can have very similar ion mobilities which in turn can significantly limit detecting and identifying low levels of the targeted chemical and/or biological molecules in the sample.

The present state of the art ion mobility spectrometers lack the ability to directly reduce the occurrence of interfering chemical and/or biological molecules in a sample's analysis. It is the purpose of this invention to overcome these obstacles by making the use of a cross-directional gas flow in a drift tube and/or using a segmented drift tube for pre-separation.

SUMMARY OF THE INVENTION

The present invention relates to, a cross-directional drift tube design for an ion mobility spectrometer wherein the drift gas flow is in a direction that is substantially neither parallel nor antiparallel to the drift axis of ions. A cross-directional drift tube with one or more drift segments allow rapid drift tube clean up and flexible drift media control. A segmented drift tube is used for pre-separation of complex sample before separating samples in the sub-sequential drift segments. The cross flow design and segmented drift tube can also be used together for enhanced separation performance. In another aspect of the present invention, at least one chemical modifier is added to the drift gas in a cross-directional gas flow that interacts selectively with at least one component of the sample in a drift tube. The component may be impurities and/or interferences in the sample whereby the chemical modifier enhances sample resolution by shifting the components drift times. The chemical modifier interaction forces, may include hydrogen bonding, dipole-dipole, and steric hindering effects, but are not limited to only these.

The present invention also relates to various aspects of Multi-Dimensional Ion Mobility Spectrometry (MDIMS) methods and apparatus. In various embodiments, the MDIMS of the present inventions differentiate themselves from conventional ion mobility spectrometry (IMS) by innovatively integrating multiple ion mobility based separation steps in one device. In various embodiments, the present invention provides higher resolution and higher sensitivity than conventional IMS devices and operational approaches. Various embodiments of the present invention provide an integrated multiple dimensional time-of-flight ion mobility spectrometric system that ionizes, separates, and detects chemical species based on their ion mobilities. These systems generally include: (a) at least one ionization source, (b) at least two drift regions, and (c) at least one ion detection device. In various embodiments, these systems separate ions in one drift dimension under one set of drift conditions; and subsequently, the separated ions are introduced into a higher dimension for further separation under the same or a different set of drift conditions. In various embodiments, the separation process can be repeated for one or more additional drift dimensions. Also, in various embodiments, the first drift dimension is used as one or more of an ionization source, reaction region or desolvation region, and drift region for the system. For example, in various embodiments, the electric field in the first drift dimension (first drift tube) can be used as a desolvation region for charged droplets.

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

BRIEF DESCRIPTION OF THE DRAWINGS

FIGS. 2A and 2B are schematic drawings of various embodiments of a multi-dimensional ion mobility spectrometer of the present inventions having two perpendicular electric field regions, where

FIGS. 8A-8C illustrative various embodiments of a one MDIMS configuration choice for a portable three dimensional instrument according to various embodiments of the present inventions.

DETAILED DESCRIPTION OF VARIOUS EMBODIMENTS

Unless otherwise specified in this document the term "ion mobility based spectrometer" is intended to mean any device that separates ions based on their ion mobilities and/or mobility differences under the same or different physical and/or chemical conditions, the spectrometer may also include detecting the ions after the separation process. Many embodiments herein use the time of flight type IMS as examples; the term ion mobility based spectrometer shall also include many other kinds of spectrometers, such as differential mobility spectrometer (DMS) and field asymmetric ion mobility spectrometer (FAIMS). Unless otherwise specified, the term ion mobility spectrometer or IMS is used interchangeable with the term ion mobility based spectrometer defined above.

The devices and methods of the present inventions make use of "drift tubes." The term "drift tube" is used herein in accordance with the accepted meaning of that term in the field of ion mobility spectrometry. A drift tube is a structure containing a neutral gas through which ions are moved under the influence of an electrical field. It is to be understood that a "drift tube" does not need to be in the form of a tube or cylinder. As understood in the art, a "drift tube" is not limited to the circular or elliptical cross-sections found in a cylinder, but can have any cross-sectional shape including, but not limited to, square, rectangular, circular, elliptical, semi-circular, triangular, etc.

Neutral gas is often referred to as a carrier gas, drift gas, buffer gas, etc. and these terms are considered interchangeable herein. The gas is at a pressure such that the mean free path of the ion, or ions, of interest is less than the dimensions of the drift tube. That is the gas pressure is chosen for viscous flow. Under conditions of viscous flow of a gas in a channel, conditions are such that the mean free path is very small compared with the transverse dimensions of the channel. At these pressures the flow characteristics are determined mainly by collisions between the gas molecules, i.e. the viscosity of the gas. The flow may be laminar or turbulent. It is preferred that the pressure in the drift tube is high enough that ions will travel a negligible distance, relative to the longitudinal length of the drift tube, before a steady-state ion mobility is achieved.

The axis of the drift tube along which ions move under the influence of the electrical drift field is referred to herein as a drift axis. The drift axis is often, but not necessarily, a longitudinal axis of the drift tube.

As used herein, the term "analytical instrument" generally refers to ion mobility based spectrometer, MS, and any other instruments that have the same or similar functions. Unless otherwise specified in this document the term "mass spectrometer" or MS is intended to mean any device or instrument that measures the mass to charge ratio of a chemical/biological compounds that have been converted to an ion or stores ions with the intention to determine the mass to charge ratio at a later time. Examples of MS include, but are not limited to: an ion trap mass spectrometer (ITMS), a time of flight mass spectrometer (TOFMS), and MS with one or more quadrupole mass filters The phrase "and/or," as used herein in the specification and in the claims, should be understood to mean "either or both" of the elements so conjoined, i.e., elements that are conjunctively present in some cases and disjunctively present in other cases.

Unless otherwise specified in this document the term "chemical and/or biological molecule" is intended to mean single or plurality of particles that are, either charged or not charge, derived from atoms, molecules, particles, and subatomic particles.

In various aspects, the present invention provides multi-dimensional ion mobility spectrometry (MDIMS) systems, preferably with multi-dimensional electric field designs in one integrated spectrometer, and methods of operating such systems. In various embodiments, the MDIMS systems and/or methods provide improved sensitivity and resolution compared to conventional single dimension drift tubes. In various embodiments, improved sensitivity can be achieved by using the first dimension as an ion storage region to improve system duty cycle. In various embodiments the MDIMS systems and/or methods provide improved mobility resolution. In various embodiments, improvements can be achieved by the use of drift regions which can further separate ions that are or have already been separated based on their mobilities. In various embodiments, as ion species are being separated in the first dimension, the columbic repulsion among them is reduced by transferring them to a second IMS dimension (e.g., using a kickout pulse). Thus, in various embodiments, higher mobility resolution can be experienced in the second dimension. In various embodiments, the first dimension can be used as an ion reaction region where further ion conversion can be achieved. In various embodiments of a MDIMS, and appropriate electric field application, a MDIMS can be used to detect both positive and negative ions substantially simultaneously.

Prior to further describing various detailed embodiments of the present inventions, it may be helpful to a fuller understanding thereof to discuss various embodiments of the apparatus and methods of the present inventions in the context of one embodiment of a three dimensional MDIMS device.

Figures 1A, 1B:
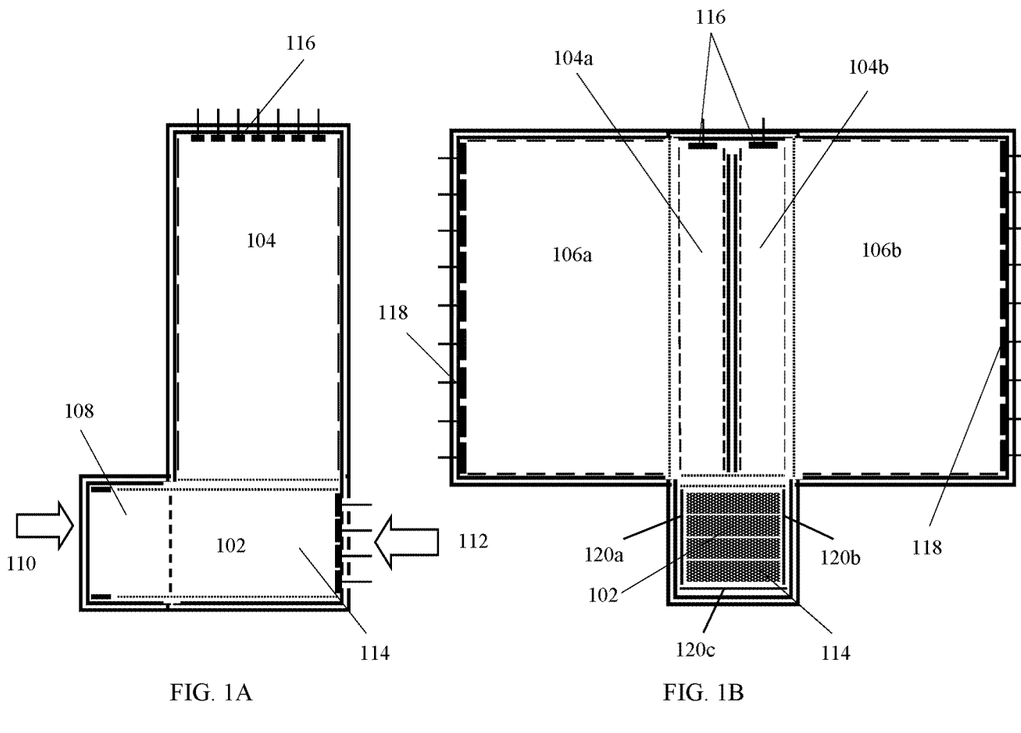
FIGS. 1A and 1B schematically shows cross-sectional views of an embodiment of a three dimensional multi-dimensional ion mobility spectrometer (MDIMS) device of the present inventions.
Figure 1C:
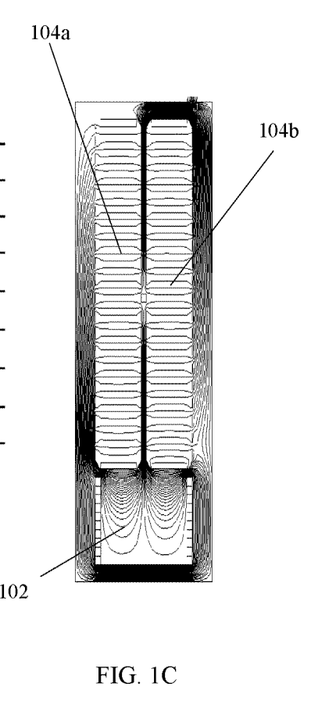
FIG. 1C shows simulated electrical potential lines within the first and second dimensions of IMS during a "kick-out" of ions from the first to second dimension. The second dimension can be used for, for example, single and/or dual polarity mode operation.

FIGS. 1A-1C illustrate various embodiments of a three dimensional MDIMS system. FIG. 1A is a side view of a first dimension drift region 102 and a second dimension drift region 104. FIG. 1B shows a side-view of the second dimension drift region 104 and a third dimension drift region 106. In FIGS. 1A-1C, the second dimension comprises two drift tubes 104a, 104b, and there is a separate third dimension drift tube 106a, 106b associated with each of the second dimension drift tubes. The second dimension 104 can be used for single or dual polarity mode operation. In various embodiments of the MDIMS, it is understood that a preferred embodiment is to arrange the drift axis of each dimension in orthogonal geometry, however, the drift axis can be arranged in parallel, anti-parallel or with an angle in between to achieve similar results.

It is to be understood, that the electrical drift field strength-to-gas number density ratio (E/N value, often expressed in units of Townsend) in all IMS dimensions of the present MDIMS apparatus and methods is chosen to establish a steady-state drift environment, sometimes referred to as a low field environment.

With the MDIMS of the present inventions, the ion mobility spectrum can be represented, e.g., in a 2-D or 3-D plot, and can use a non-linear detection window. Chemicals can be identified in their 1-D, 2-D or 3-D mobility profile. This mobility profiling method can provide additional information and thus, can provide greater confidence for chemical (e.g., explosive) identification.

In various embodiments a Dual Polarity Ion Extraction (DPIE) operational mode can be conducted using the first dimension 102 as a flow through cell where both positive and negative ions are brought into the first drift chamber by gas flow while the drift voltage in the first dimension is turned off (i.e., substantially no drift field is present). At a predetermined time ions are and kicked out into the second dimension, preferably such that the positive and negative ions in the first dimension are substantially simultaneously extracted into two separated drift chambers 104a, 104b in the second dimension 104. After ions are separated in the second dimension 104, they can be further separated and detected in the third 106 or higher dimensions.

In various embodiments, ionized samples are guided into and/or formed in the first drift region 102 and subject to a first order separation based on mobility (resembling conventional IMS). At a given predetermined time, separated ions in the first dimension (first drift tube) are kicked out into the second drift dimension 104 drift region where they are separated in the direction that is substantially perpendicular to the first drift direction. The same process can be continued in the higher dimensions if desired with further dimensions of IMS.

FIG. 1C shows simulation results of the electric field distribution of a DPIE process in a Dual Second Dimension Ion Mobility Spectrometer (DSDIMS) of FIGS. 1A and 1B. In FIG. 1C, the three walls in the first dimension 102 (left, bottom, and right) are at 1,000 V and the gate grids are set at 0 V and 2,000 V respectively. The equi-potential lines are shown in the figure. The sample gas flow used to carry ions through the first dimension can be exhaust, e.g., behind the first dimension detector 114. After ions are separated in the second dimension 104, a kick out voltage can be applied to bring the separated ions into the third dimension 106. In a continuous sample detection scenario, the sequence will repeat. For a chemical mixture that may form both positive and negative ions, various embodiments of the DPIE technique can extract more than 50% of both positive and negative ions into the second dimension.

Figure 7A:
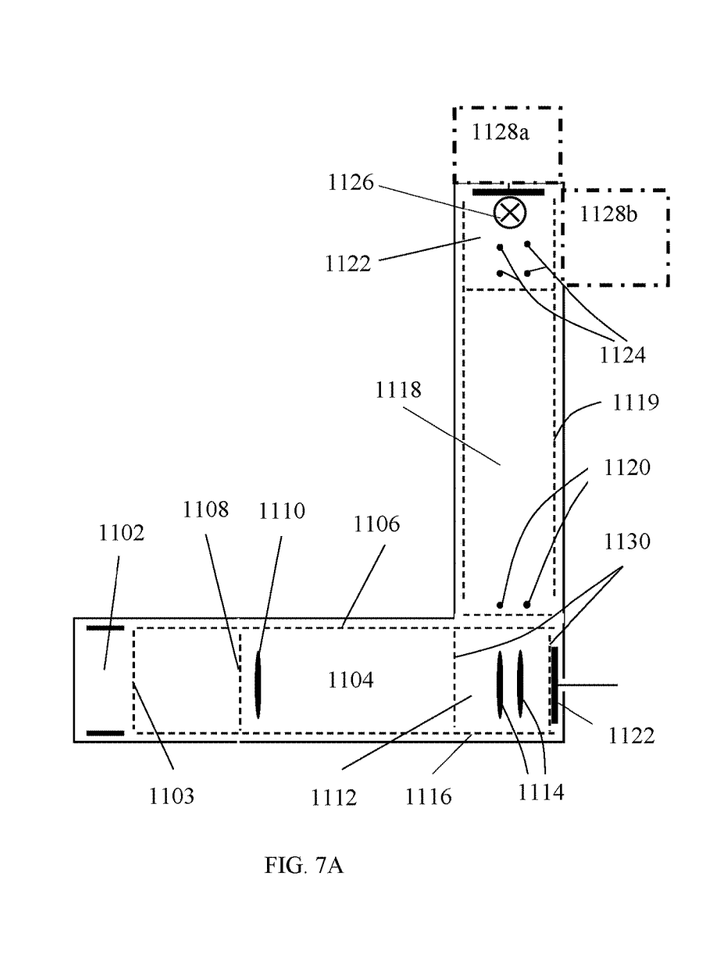
FIGS. 7A and 7B are schematic drawings of various embodiments of a MDIMS, for example, for SII and MS'' implementation.
Figure 7B:
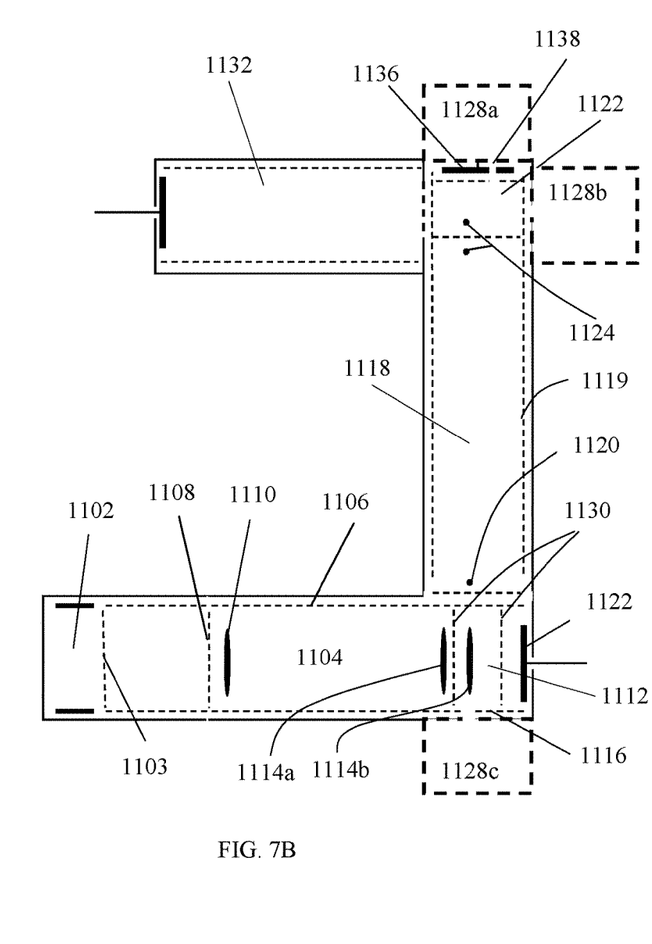

In various embodiments, the MDIMS devices can transport ions between each dimension without significantly losing resolving power. Referring to FIG. 7, in various embodiments, when ions are separated in the first dimension; they can look like a thin plate 1110. To move them into the direction that is perpendicular to the first dimension, voltages are changed on the appropriate electrodes (typically an electrode opposite the inlet, the inlet itself, or both) within a microsecond range. The electric field during these kick out moments can be manipulated to create temporary high and low electric field zones. The thin plate 1110 in the high field zone can be compressed into a thin line 1120 in the low field zone of the second dimension.

Figures 2A, 2B:
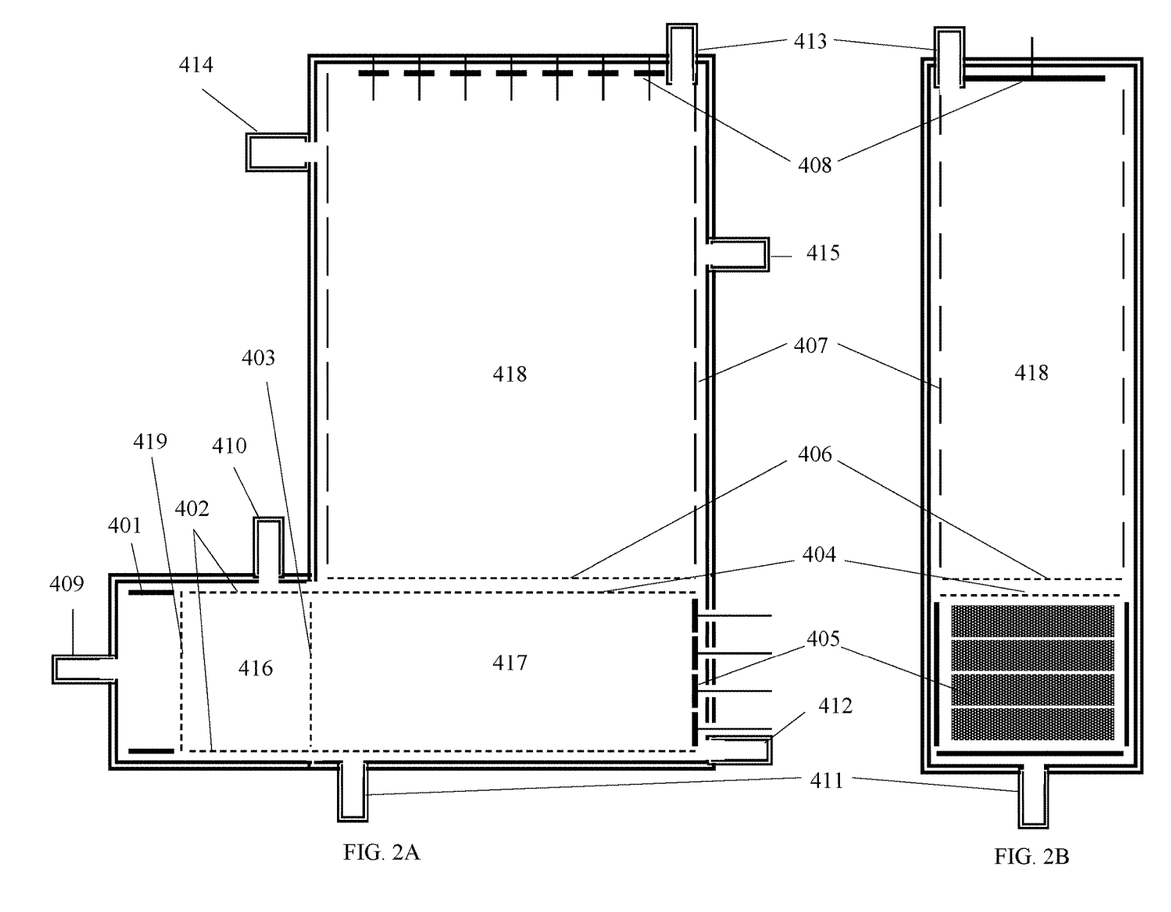
FIG. 2A depicts a front cross-sectional view and FIG. 2B depicts a side cross-sectional view of the MDIMS.

Referring to FIG. 2, provided is a schematic drawings of various embodiments of a multi-dimensional ion mobility spectrometer having dual second ion mobility dimensions. FIG. 2A is a front cross section view and FIG. 2B is a side cross sectional view of the MDIMS.

In various embodiments, a MDIMS comprises an ionization source 401 to, for example, (a) generate reactant ions and a reaction region where reactant ions can react with samples and form product ions to be detected for sample identification; (b) generate sample ions for detection, (c) or both. The reaction region can be guarded by ion guides 402 that generate a substantially continuous electric field to, e.g., lead the ions to the first dimension drift region 417 (first drift tube).

In Multiple Step Separation (MSS) mode operation, a pulse of ions are generated by opening an ion gate 403, to introduce them into the first dimension drift region 417; the ions are separated based on their mobilities under the guidance a substantially continuous electric drift field in the first drift tube 417. In one embodiment, the electric field is generated by a series of ion guides 404. Each ion guide can comprise one or more electrodes; and different voltages can be applied on each electrode to establish the potential difference across the first drift tube. For example, FIG. 2B shows four electrodes used for each first dimension ion guides.

In various embodiments of MSS mode operation, as a first group of ions reaches the first dimension detector matrix 405, a kick out voltage can be applied to generate a high electric field that is perpendicular to the first dimension drift field, thus the ions separated in the first dimension are moved into the second dimension drift region 418. An electric field separator screen 406 can be used to help define the electric field in the second dimension. Ions introduced into the second field will continue to drift across the second dimension drift region 418 and further separation can be achieved. The ion guides 407 in the second dimension 418 can be arranged similarly to the first dimension ion guides 404, for example, if a third dimension of separation is desired. If a third dimension is desired, complete square electrodes can be used as the ion guides. Ions separated in the second dimension can be detected by the detector 408. The detector can comprise multiple detectors according to required special resolution of the spectrometer or a single detector.

In various embodiments, a partial kick out operation can be performed when ions are introduced from the first dimension to the second dimension. If only a portion of the ions are kicked out, the mobility measurement in the first dimension can be resumed after the kick out. Thus, an ion mobility spectrum can also be acquired independently in the first dimension. As a complete kick out can increase the sensitivity in the second dimension, alternating between these operation methods can be beneficial. In addition, a clean up operation, e.g., remove all ions in the drift chambers by an applied "kick out" electric field for an extended period of time, can also be added between detection cycles.

The low dimension operation of the spectrometer can be used as fast screening method to generate a quick survey of the ionic species from the ionization source. In combination with the normal operation of the MSS mode, the survey of the ionic species can be used as an index to guide upper dimension operations. The survey mode operation can also be used to selectively kick out ions of interest, simplifying higher dimension spectra, and saving total analysis.

Different drift/separation conditions can be established independently for each dimension, e.g., different drift gases may be used in each dimension or different drift gas temperatures in each dimension.

The MDIMS can be operated in a fashion where a number of multiple dimensional positive ion mobility data is collected followed by a number of multiple dimensional negative ion mobility data. The sequence can be realized, e.g., by alternation the polarities of electric fields in the spectrometer.

During MSS mode operation, the directions of the drift gas flow can be set to be counter to or across from the ion movement. For example, in various embodiments, gas port 413 can be used as the second dimension drift gas inlet and port 412 as the first dimension drift gas inlet, port 409 as the sample flow inlet and port 410 as purge gas outlet. The other ports are preferably plugged or remove when they are not in use. The size of each port can be selected depending on the flow required to achieve the flow pattern inside the spectrometer and preferably the drift flow sweeps the entire drift region and removes excessive sample molecules and any other reactive neutral molecules.

Figure 3:
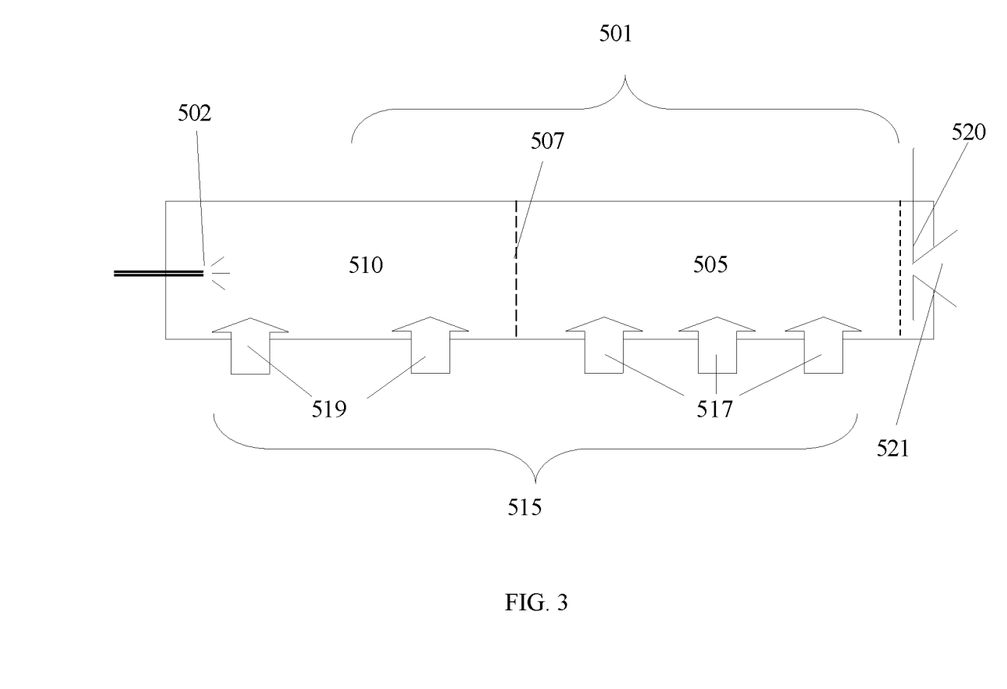
FIG. 3 shows an IMS using a cross-flow drift medium design.

One aspect of the present invention is a method and apparatus for using a cross flow IMS apparatus for effectively removing neutral molecules from drift tube. In a time of flight type ion mobility spectrometer, the cross gas flow is used in a manner that is similar to conventional uni- or counter-directional drift gas flow, the drift gas flow does not substantially affect the ion separation along the drift axis. Compared to prior art counter- and uni-direction drift flow design, the cross flow design allows neutral molecule(s) to only travel a short distance and less time in a drift region. A non-limiting example is shown in FIG. 3 where a drift segment is used. However more than one drift segment can be used. The drift tube 501 comprises: an ionization source 502, a desolvation region 510 and an analytical segment (drift region) 505 separated by an ion gate 507. After a sample is introduced into one end of the IMS (in this particular case an ESI source 502 is used, any other ionization source could be used), the ionized sample and solvent ions are formed in the desolvation region 510, a narrow pulse on the ion gate 507 introduces the ion mixture into the separation segment 505. This configuration has the drift gas flow 515 (comprise of drift flow for desolvation 519 and separation 517) in a direction that is substantially perpendicular to the drift axis of the ions; the drift axis generally represent the averaged ion path in the drift tube. With cross flow configuration, neutral molecules that travel with the drift and desolvation gas flow are not mixed across desolvation and drift region. Neutral fragments that are generated during drift and desolvation process in the drift tube are effectively removed from the drift tube avoiding further gas phase ion molecular interaction in the drift tube. The cross-directional drift gas can be in a direction that is between greater than 0° to less than 180° to that of the drift axis of the ions. The cross-directional drift gas is applied to a substantial portion of the desolvation and/or drift region. In many cases the cross-directional drift gas is applied over the entire drift axis. In addition, the cross-directional gas flow 515 can be a drift medium that comprises various components. The components may be a plurality chemical modifiers and/or a plurality of drift gases. The cross-directional flow can comprise different drift medium in the different segments and/or regions of the IMS. For example, as shown in FIG. 3, drift gas flow 519 can comprise the same and/or different drift medium as drift gas flow 517.

In various embodiments, the cross flow configuration for the IMS can be combined with counter or uni-direction flow configurations. For example, if the drift region has a cross flow arrangement as shown in FIG. 3, a portion the drift flow could be exhausted into the desolvation region and then pumped away from the end of the desolvation region, given the desolvation region is using a counter direction gas flow arrangement.

Figure 4:
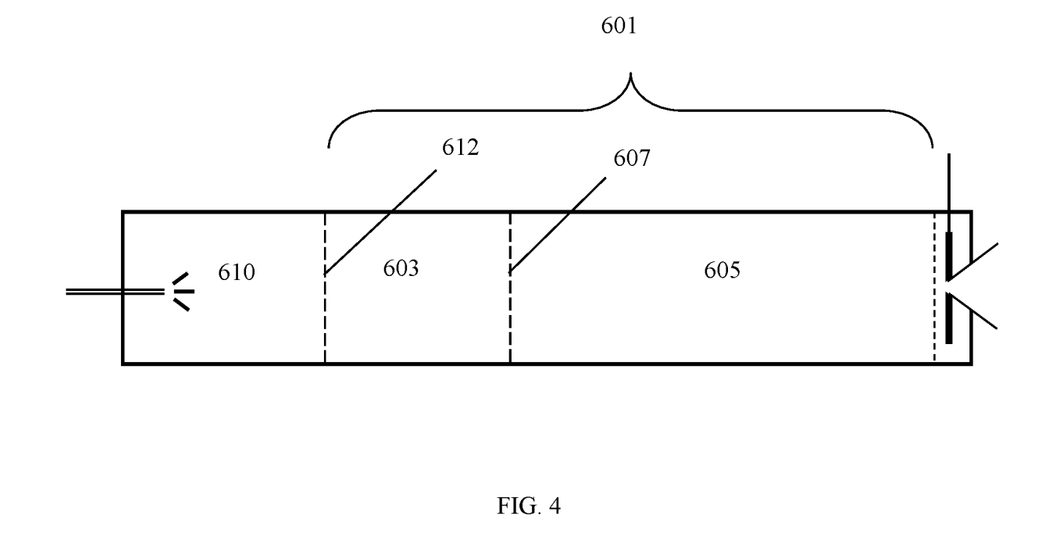
FIG. 4 shows an IMS using a segmented drift tube for pre-separation.

In another aspect of the present invention a multiple segmented IMS apparatus is used for pre-separation of the sample. A non-limiting example is shown in FIG. 4 where two drift segments are used. However more than two drift segment can be used. The drift tube 601 comprises: a pre-separation segment 603 and an analytical segment 605 separated by an ion gate 607. The pre-separation segment 603 resembles the pre-separation column used in chromatography. After a sample is introduced into one end of the IMS (in this particular case an ESI source is used, any other ionization source could be used), the ionized sample and solvent ions are formed in the desolvation region 610, a narrow pulse on the first ion gate 612 introduces the ion mixture into the pre-separation segment 603. The second ion gate 607 is timed to open so that only components of the sample are allowed to enter the analytical segment 605. Elimination of the solvent avoids ion-molecule reactions in the analytical segment 605 of the drift tube 601.

In various embodiments the two gate IMS apparatus and method, the first gate transmits packets of ions and these ions move to the second gate. Part of the ions from the first gate will be transmitted through to the second gate and the transmitted ions will be further separated through the drift region. Ions at the second gate have low density and the space charge effect can be reduced and the IMS will have enhanced separation. The IMS separated ions can be detected by a faraday plate and can be transported to a mass analyzer for further analysis.

In another embodiment of the two gate IMS apparatus and method, the first gate transmits narrow ion packets. Higher ion mobility ions take a shorter time to get to the second gate than lower mobility ions. By controlling the second gate timing, certain mobility ions are transmitted through the second gate. The first gate can be controlled to transmit the second, third, fourth, etc. ion packet before the first packet reaches the detector. The first and second gate will be operated synchronously with different start-on time and width of opening. Ions transmitted through the second gate will be separated while traveling through the drift region and being detected by the detector or being transported to the mass analyzer. The first gate opening will have a specific period which was determined not to mix ions of different packets. A grid in front of the detector can be replaced by an exit gate to further limit the ions with specific ion mobility.

A segmented drift tube with multiple ion gates can be used with cross flow design for easy application of different drift media in different segments, however, segmented drift tube design could be used with one drift media, and/or with conventional uni- or counter-direction drift gas flow designs.

Figure 5:
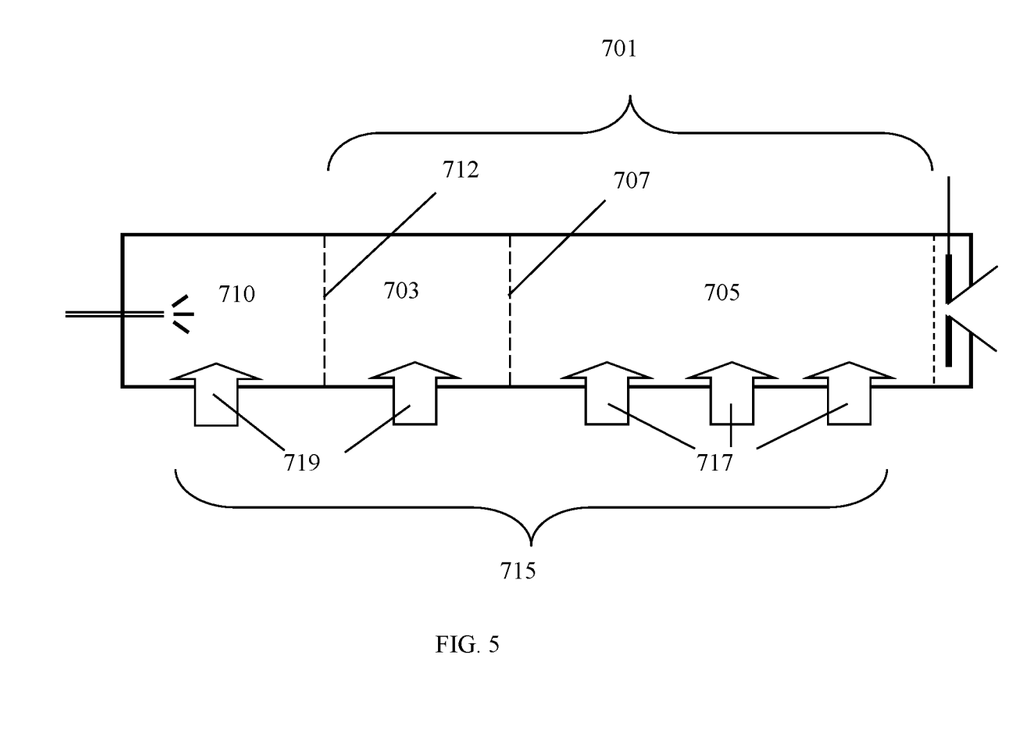
FIG. 5 shows an IMS using a cross-flow drift medium design combined with a segmented drift tube.

In another aspect of the present invention a multiple segmented planar IMS apparatus combined with a cross flow can be used to enhance separation of components of a sample. In this case, solvent ions as well as solvent neutrals are eliminated from the analytical segment. A non-limiting example is shown in FIG. 5 where two drift segments are used. However more than one drift segment can be used. The drift tube 701 comprises: a pre-separation segment 703 and an analytical segment 705 separated by an ion gate 707. The pre-separation segment 703 resembles the pre-separation column used in chromatography. After a sample is introduced into one end of the IMS (in this particular case an ESI source is used, any other ionization source could be used), the ionized sample and solvent ions are formed in the desolvation region 710, a narrow pulse on the first ion gate 712 introduces the ion mixture into the pre-separation segment 703. The second ion gate 707 is timed to open so that only components of the sample are allowed to enter the analytical segment 705. Elimination of the solvent avoids ion-molecule reactions in the analytical segment 705 of the drift tube 701. This configuration has the drift gas flow 715 in a direction that is substantially perpendicular to the drift axis of the ions, the drift axis generally represent the averaged ion path in the drift tube. With cross flow configuration, neutral molecules that travel with the drift and desolvation gas flow are not mixed across desolvation and drift region. Neutral fragments that are generated during drift and desolvation process in the drift tube are effectively removed from the drift tube avoiding further gas phase ion molecular interaction in the drift tube. The cross-directional drift gas can be in a direction that is between greater than 0° to less than 180° to that of the drift axis of the ions. The cross-directional gas flow can be a drift medium that comprises various components. The components may be a plurality chemical modifiers and/or a plurality of drift gases. The cross-directional flow can comprise different drift medium in the different segments of the IMS. For example, as shown in FIG. 5, drift gas flow 719 can comprise the same and/or different drift medium as drift gas flow 717.

A separation apparatus, comprising: an ionization source ionzing a sample that contain a least one component in front of an ion gate; a drift tube that has a drift axis along which ions are separated; and a drift flow in a direction that is greater than zero but less then one hundred and eighty degrees from the drift axis. The apparatus can further comprise at least one chemical modifier that is added to the drift flow for separation enhancement. In one embodiment, a separation apparatus comprising: an ionization source ionizing a sample that ionizes samples; a drift tube has a drift axis along which ions are separated, wherein the drift tube has greater than or equal to, two drift segments in which the ions are separated, and a ion gate that is placed between drift segments. The separation apparatus may further comprises at least one chemical modifier that is added to the drift flow.

In another embodiment of the present invention, a chemical modifier can be added to different segments or regions of the IMS in order to target specific interactions with various components of the sample. Two or more segments can be used, but for simplification a two segment design will be discussed. Therefore two or more different chemical modifiers can be used in the IMS without substantially interfering with each other. 0 to 100% of modifier can be used in each of the different segments or regions of the IMS. The cross flow drift design is one way to add the modifier, but it is not necessary to use cross flow in order to add the modifiers to each segment or region in the IMS. The different segments or regions can be isolated from each other by a number of ways which include but are not limited to; using gates in between or a small opening, slits or pinholes. In this configuration, a modifier that targets one functional group can be added to the first region of the IMS and a second type of modifier can be added to the next region that interacts with a different functional group. Unlike previous methods where a transforming agent, immobilizing agent, or chiral molecule is added to the sample components prior to ionization, in this process, the sample components are modified in the drift tube in discrete sections according to the desired interaction. For example, in order to separate a pair of enantiomers in a sample, a chiral modifier added to the cross flow drift gas in the first region of the drift tube which forms diastereomer components that are then interacted by a second modifier added to the cross flow drift gas in a second region of the drift tube to enhance separation.

Figure 6:
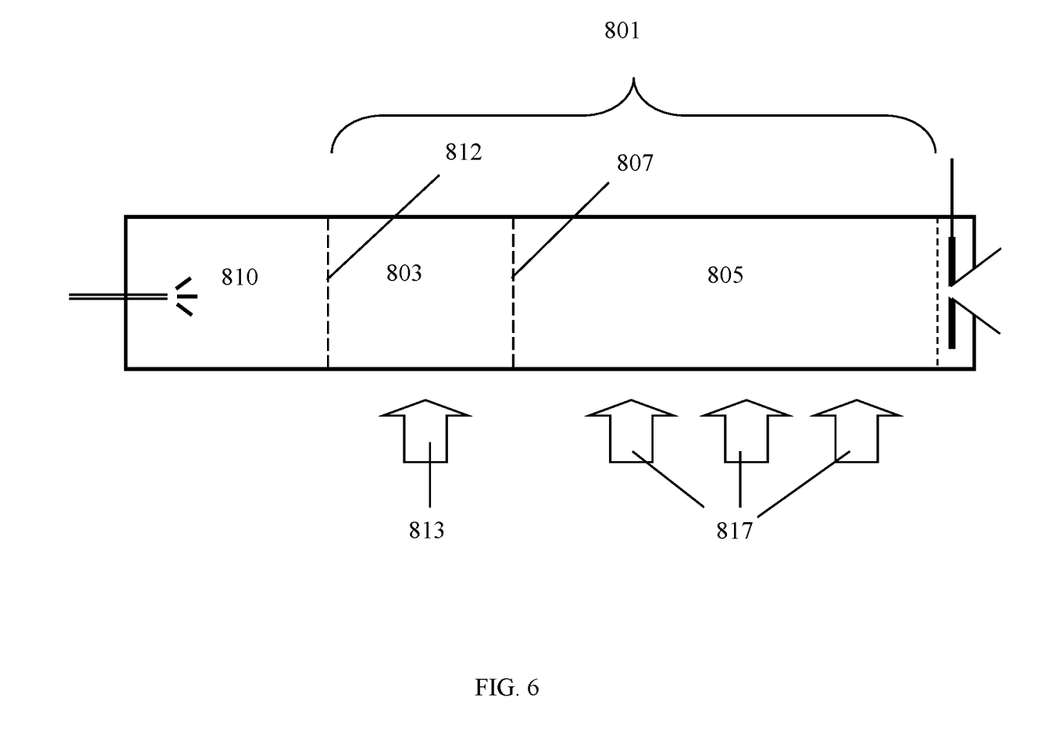
FIG. 6 shows an IMS using a segmented drift tube design with cross flow for added specific modifiers to each segmented region.

FIG. 6 shows an IMS where the sample is ionized in the desolvation region 810. The drift tube 801 consists of two regions 803 and 805 that have an applied electric field (not shown) and are separated by a gate 807. Another gate separates the desolvation region 810 from the drift tube 801 with a gate 812. In the case of a sample that has two enantiomer components, this enantiomer pair is ionized in the desolvation region 810 and is then allowed to travel into the first separation region 803 whereby 0-100% of a chiral modifier is added to the cross drift flow 813 which interacts with the enantiomer pair. Diastereomers are then formed and are let into the second separation region 805. These diastereomers are then separated in the second separation region with enhanced separation by using 0-100% of a modifier that is added to the cross drift flow 817.

One embodiment of this invention is to rigidify the molecules (limit the number of conformations) by adding an immobilizing agent to the first drift region of the drift tube. The immobilizing agent stabilizes the gas phase structure of analytes in order to enhance the interaction of the modifier in the second region of the drift tube in order to enhance separation. In variety of embodiments, a modifier that can frame (affix) the higher order structure of a gas phase analyte molecule is used to achieve well-defined gas phase mobility of the analytes. Forming complexes with metals and/or other molecules is a non-limiting example of this method. Another embodiment of this invention is to add at least one transforming agent as a modifier to the first drift region, which bonds/binds (interacts) to at least one component of the sample. The bonding interactions or attraction forces may include; hydrogen bonds, van der Waals forces, dipole-dipole, steric hindering effects, coordinate covalent bond, metallic bond, ionic bond, non-covalent bond, covalent bond, weak covalent nature, antibonding, short-lived metastable, clusters, but is not limited to only these. A second chemical modifier is added to the second region of the drift tube that interacts selectively with the component of the sample and/or transforming agent which resolves/separates the component from other components of the sample based on their measured ion mobility characteristics.

A separation method, comprising ionizing a sample with at least one component; separating the ionized sample along a drift axis of a drift tube, and proving a drift flow in a direction that is greater than zero but less then one hundred and eighty degrees from the drift axis. The separation method may further comprise removing neutral molecules in the drift tube along with the drift flow; the neutral molecules could be, but not limited to, one component of the sample; fragment of a sample molecule; contaminants in the apparatus. In one embodiment, a separation method comprising: ionizing a sample with at least one component; providing the sample to an ion mobility based spectrometer with greater than or equal to, two drift segments separated by an ion gate between the drift segments; transporting the ionized sample as a ion packet along a drift axis; and pre-separating the ion packet in one of the drift segments prior to further separation in other separation segments. This separation method may further comprises; adding at least one chemical modifier to a drift gas flow that is in a direction to that of the drift axis of the ions that is between greater than 0 degrees to less than 180 degrees.

In various embodiments, the drift gas can be supplied to the higher dimension in the direction that is in substantially parallel to the lower dimension. For example, port 415 can be used as the second dimension drift gas inlet, port 414 as the second dimension drift gas outlet, port 412 as first dimension drift gas inlet, and port 410 as the first dimension drift gas outlet. Under linear flow conditions and the parallel flow pattern, for example, limited mixing of drift gas near the dimension interface is expected.

In SBA mode operation, the sample is provided into the spectrometer through port 409. Through the ionization source 401, the ionized samples are brought into the first dimension drift region 417 by gas flow. In case where only a single polarity of ions is of interests, the flow can be purged from port 412 or port 411. In various embodiments of the SBA operational mode, the first dimension drift tube can be used as ion storage device to, e.g., increase the duty cycle of the device.

In various embodiments of Continuous First Dimension Ionization (CFDI) mode operation, the samples are introduced to the spectrometer from port 412 as pulses of gas. The sample gas pulse can be formed in a wide variety of ways, for example, by thermally desorbing chemicals from a surface, as the eluent of a chromatographic separation, by pumping the sample into the spectrometer for a short period of time, introduction through a pulsed valve, etc. In many embodiments, the flow under a linear flow condition, and a "plug" of gas phase sample is directed from the port 412 towards the ionization source 401 by gas flow. Pulses of reactant ions (preferably at high density) are generated by the ionization source 401 and guided by the electrical drift field to drift towards the sample "plug". As the pulse of reactant ions and samples intercept in the first dimension 417, a portion of the samples are ionized. As the sample encounters multiple reactant ion pulses in the same acquisition period, chemicals in the sample "plug" are ionized. Chemicals with different properties (e.g., charge affinity) can thus be separated and detected at different locations on the detector matrix 408. This gas phase titration method can improve ionization efficiency of ion mixture where chemicals with different properties coexist. By this means chemicals that can not be detected in conventional IMS can be detected.

In various embodiments, the CFDI can also be performed in the reaction region 416, shown in FIG. 2. A plurality of pulses of reactant ion is generated by pulsing ion gate 419 while pulsed sample are introduce to the spectrometer from gas port 410. In this implementation, ion gate 403 is removed or kept open. Pulse of ions generated in the reaction region 416 are separated in first dimension drift region 417, and then the separated ions are extracted in higher dimension drift region 418 for further ion mobility analysis if so desired. In various embodiments, the CFDI method can be used as an independent ionization source directly interfaced to spectrometers, such as differential mobility spectrometer, ion mobility spectrometer or a mass spectrometer, either inline or perpendicular to the direction drift electric field. In embodiments where CFDI is used for a single IMS, the shutter grid 419 will be used instead of grid 403. The ionized chemical species continue to drift in drift region 417 after formation in the reaction region 416. Similarly, interfaces to other spectrometers, such as differential ion mobility spectrometers and mass spectrometers, can also be realized by placing the sample inlet of these instruments directly after the reaction region.

The CFDI mode can be preformed using reactant ions with different chemical properties. For example, modifying the ion chemistry using a variety of chemical reagents that react with initial reactant ions can generates reactant ions with different chemical properties. These ionic species can be used, e.g., to ionize samples introduced to the spectrometer. Similar effects can be achieved, e.g., by using an ionization source that can generate different ionic species or charged particles/droplets. In various embodiments, altering the ionization chemistry can be used to achieve substantially selective ionization of targeted chemicals in the sample. For example, a series of ion pulse with different chemical properties can be used to ionize chemicals with compatible ionization properties in the sample.

In Selective Ion Introduction (SII) mode operation, one or multiple groups of selected ions are kicked out into a higher dimension. The selective kick out can be realized by applying a kick out voltage at a predetermined time to the region where ions of interests are traveling through at a given timing. In various embodiments, the kick out pulse is not necessarily applied to a selected region of the lower dimension, but the higher dimension drift chamber does not intercept the lower dimension only over a portion of length of the lower dimension; thus, e.g., a selected location can be designed only to allow a small group of ions to be kick out into the second dimension. A similar result as described with respect to MSS mode can be achieved by controlling the kick out timing and performing multiple acquisition cycles.

In various embodiments of MDIMS systems, the higher dimension drift region, such as the second dimension region, can be operated in different phases of drift media, e.g. gas or liquid. The liquid phase drift cell can be constructed with two parallel plates or grids instead of a conventional drift tube design. The liquid phase drift cell can be a thin layer of liquid that has an electric field across the layer. The higher order dimension drift cell has drift axis that is substantially parallel or substantially perpendicular to the first dimension drift axis. The higher dimension drift cell has multiple compartments (channels) that are substantially perpendicular to the lower dimension drift axis. The higher dimension drift cell can be used for selectively collecting samples separated in the lower dimension drift tube. The higher dimension drift cell can be further interface to other separation and detection apparatus, including but not limited to electrophoresis, chromatography, UV absorption and other spectroscopic apparatus.

In various embodiments of MDIMS systems of the present inventions, different drift gases are used in different drift tubes and/or dimensions of the MDIMS to separate ionic species in a higher dimension (e.g., a second dimension) that are not sufficiently separated in the drift gas in a lower dimension (e.g., the first dimension). It is to be understood that the drift gas can be a mixture of two or more gases. Similar separations can also be done by varying other drift chamber conditions.

FIGS. 7A and 7B show schematic examples of various embodiments that can be used to realize the SII mode operation with IMS". By reducing the physical size of the higher dimensions and controlling the timing of the kick out pulse, a selected group of ions 1114 that drifted into the kick out region 1112 can be brought into a higher dimension drift chamber 1118 where they can be further separated. The same process can be continued until the nth separation performed in different drift chambers. The geometry of the interconnected drift chambers can be two dimensional (FIG. 7B) or three dimensional (FIG. 7A), thus the number of times a higher order mobility separation can be conducted is not necessarily limited by the physical space available for the spectrometer.

In various embodiments, FIG. 7A shows schematic of a three dimensional MDIMS that illustrate SII mode operation. When gas phase sample is introduced into the reaction region of the first dimension drift tube, between ion gates 1103 and 1108, the sample is ionized by either CFDI or conventional ionization methods with reactant ions created by ionization source 1102. The sample ions mixed with reactant ions are pulsed into the first drift region 1104. Under the guidance of the electric field generated by ion guide 1106, the ion mixture separates in the first dimension. At a predetermined timing when ions of interest 1114 drift into the kick out region 1112, a kick out voltage can be applied to a set of electrodes (including a split ion guide 1116 and grids 1130) to extract ions into the second dimension. As ions 1114 are compressed in the interface between the kick out region 1112 and second dimension drift region 1118, narrow pulses of plural separated ions 1120 are created at the beginning of second dimension drift region 1118. The ions pulses 1120 are separated in the drift region 1118 that is guarded by ion guides 1119. The further separated ions 1124 are extracted from second ion kick out region 1122 into the third drift chamber that has a drift direction 1126 (pointing insider the paper) that is orthogonal to the first and second dimension. The extracted ions repeat the process described above in the third dimension or higher.

In various embodiments, FIG. 7B shows schematic a MDIMS operating in SII mode with a two dimensional structure. FIG. 7B illustrates that one peak 1114b isolated by the first dimension drift tube is extracted into second dimension, and then one peak isolated by the second dimension drift tube is extracted into the third dimension 1132 having a drift direction that is substantially perpendicular to the second dimension and substantially anti-parallel to the first dimension. In this example, the drift axes of all dimensions are on the same plane.

For example, in various embodiments, the configuration of FIGS. 7A and 7B can be interfaced to other detectors, such as a mass spectrometer. IMS-MS systems are commonly used to achieve mobility based separation before mass analysis. The interface to a mass spectrometer can be in-line with ion drifting direction behind the detector matrix, e.g. 1122 or 1136. FIG. 7B shows an interface to a mass spectrometer 1128a through an opening on the second dimension detector matrix 1138, or perpendicular to the drifting direction using a kick out pulse to push ions into the interface 1128b and 1128c. Higher ion transportation efficiency is expected in the later case.

Figure 8A:
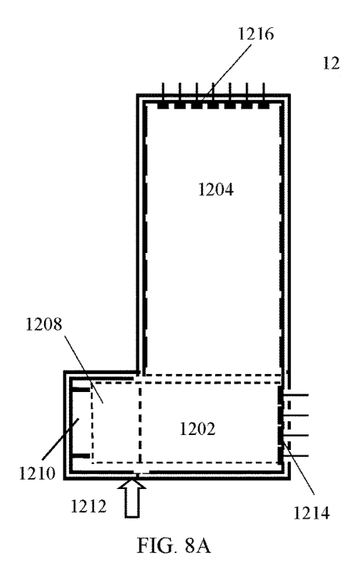
FIGS. 8A and 8B provide schematic two-dimensional cross sectional views and FIG. 8C provides a schematic three-dimensional cross-sectional view.
Figure 8B:
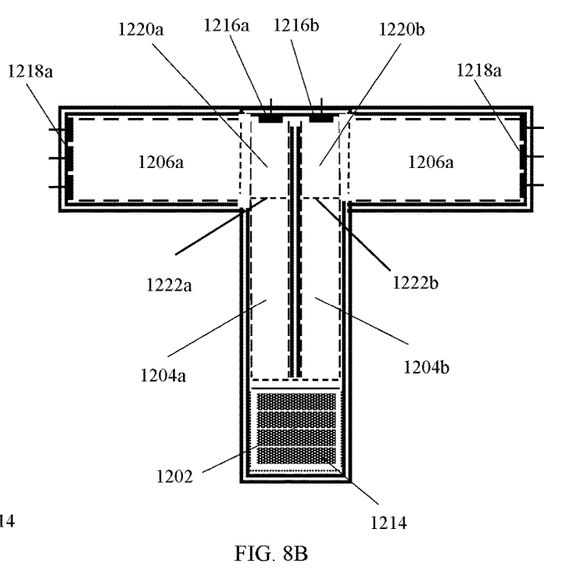
Figure 8C:
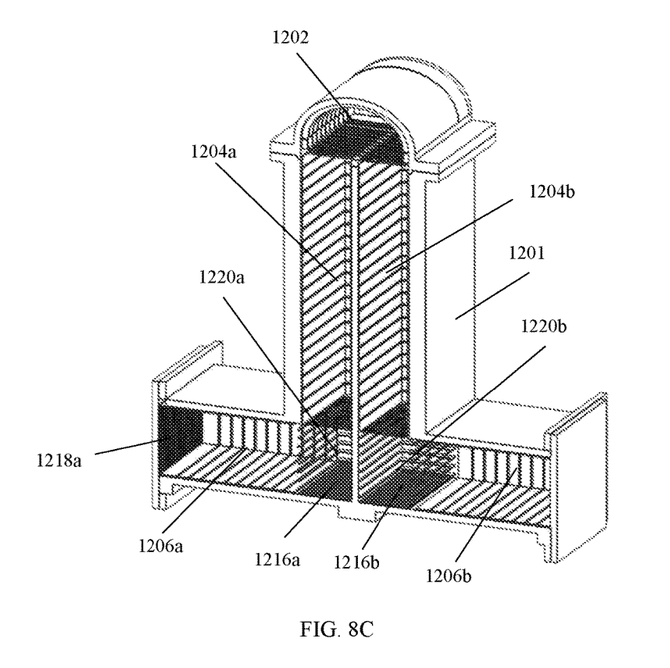

In various embodiments of the MDIMS, FIG. 8A-C shows the schematic of an example of the compact MDIMS. The device is configured with three dimensions, including one first dimension chamber 1202, two second dimension drift chamber 1204a, 1204b, and two third dimension chambers 1206a and 1206b, with a largest dimension of <10 cm. FIG. 8C is the three dimensional drawing of the MDIMS to the scales. The configuration is to realize both CFDI and DPIE with SII mode. In CFDI operation, the reactant ions are formed in ion source 1210 and pulsed into the reaction region 1208 to selectively ionize pulsed sample 1212. Ionized samples are separated in first dimension drift region 1202 and then further separated in higher dimension drift region 1204 and 1206.

Figure 9A:
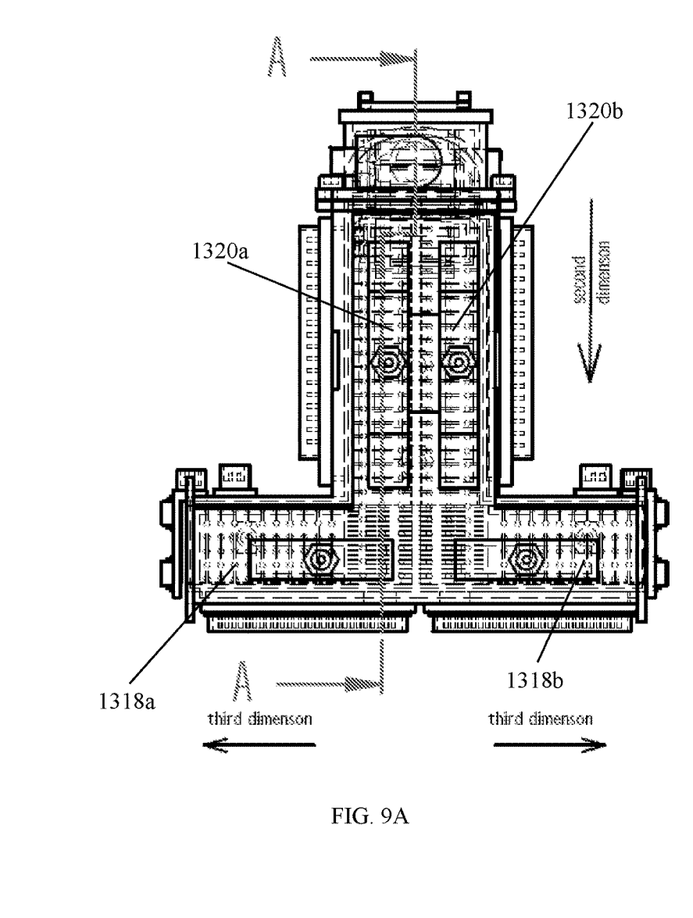
FIGS. 9A and 9B are schematic scale drawings of the MDIMS system of FIGS. 10A-10B.
Figure 9B:
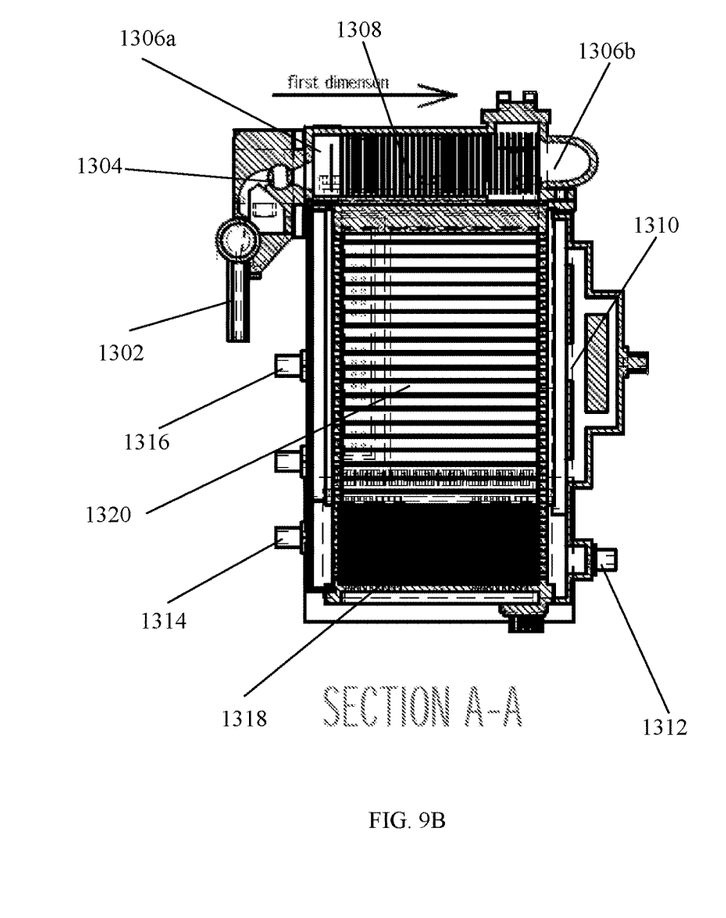

In DPIE operation, both positive and negative ions formed in the ionization source 1210 and reaction region 1208 are carried into the first dimension 1202 by carrier flow without effluence of the electric field. The positive and negative ions are extracted in to the second dimension drift chambers 1204a and 1204b, respectively. The sample ions are detected on the detector matrix in the first dimension 1214, second dimension 1216 or third dimension 1218a and 1218b depending on the instrument usage and it is software controlled. For fast screening operation, ions are detected at lower dimension detectors for high throughput. For highest resolution, ions are measure at the third dimension detectors. The engineering drawings of the configuration are shown in FIGS. 9A and 9B. The practical unit includes sample inlet 1302, sample inlet control valve 1304, ionization source 1306a and 1306b, and first dimension drift region 1308. The drift flow is deigned to sweep cross the second drift region 1320 1320b and third drift region 1318a 1318b. At drift gas inlet 1310 and 1312, a flow distribution system is used to assure even drift flow across the entire drift chambers. The drift gas is purge for port 1314 and 1316.

Figure 10A:
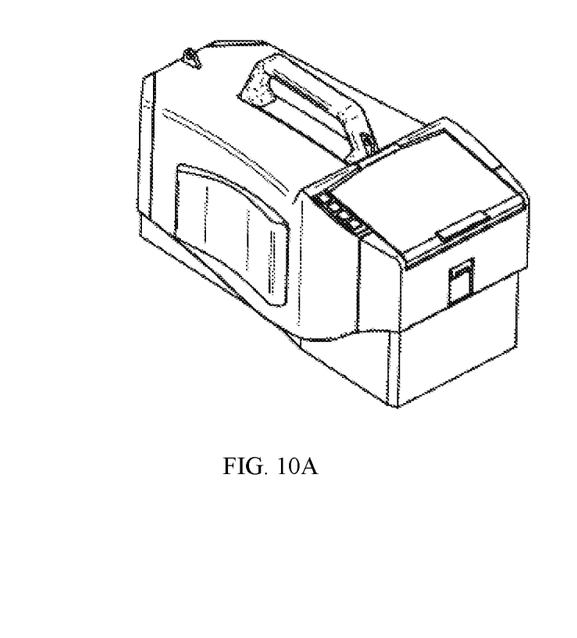
FIGS. 10A-10B are scale schematic drawings of a preferred embodiment of a portable MDIMS incorporating various embodiments of the present inventions.
Figure 10B:
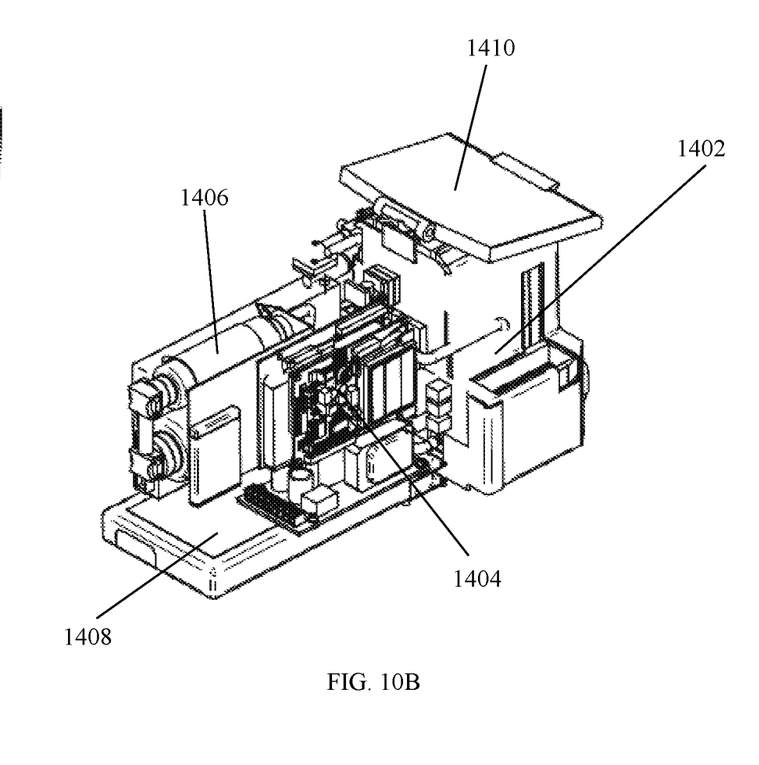

FIGS. 10A and 10B shows engineering drawings of a portable system based on the detector described in FIG. 8 and FIG. 9. The portable package include, pneumatic system 1406, electronics and computer controls 1404, user interface and display 1410, battery power 1408, and a MDIMS 1402.

A modularized design approach is preferably used in the MDIMS of the present inventions to facilitate the provision of future upgrades. For example, a different ionization source may be desired for different applications. Such sources may be, e.g., a corona discharge, electrospray ionization or desorption electrospray ionization. The provision of a modular design can facilitate the changing of the ion source.

In another aspect, the functionality of one or more of the methods described above may be implemented as computer-readable instructions on a general purpose processor or computer. The computer may be separate from, detachable from, or may be integrated into a MDIMS system. The computer-readable instructions may be written in any one of a number of high-level languages, such as, for example, FORTRAN, PASCAL, C, C++, or BASIC. Further, the computer-readable instructions may be written in a script, macro, or functionality embedded in commercially available software, such as EXCEL or VISUAL BASIC. Additionally, the computer-readable instructions could be implemented in an assembly language directed to a microprocessor resident on a computer. For example, the computer-readable instructions could be implemented in Intel 80x86 assembly language, if it were configured to run on an IBM PC or PC clone. In one embodiment, the computer-readable instructions can be embedded on an article of manufacture including, but not limited to, a computer-readable program medium such as, for example, a floppy disk, a hard disk, an optical disk, a magnetic tape, a PROM, an EPROM, or CD-ROM (or any other type of data storage medium).

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

The claims should not be read as limited to the described order or elements unless stated to that effect. While the present inventions have been described in conjunction with various embodiments and examples, it is not intended that the present inventions be limited to such embodiments or examples. On the contrary, the present inventions encompass various alternatives, modifications, and equivalents, as will be appreciated by those of skill in the art.

What is claimed is:

1. A time-of-flight ion mobility spectrometer method, comprising:
   ionizing a sample with at least one component;
   pulsing the ionized sample into a drift tube;
   separating the components of the ionized sample pulse along a drift axis of the drift tube, and;
   providing a cross drift flow substantially in a direction that is greater than zero but less then one hundred and eighty degrees from the drift axis, and
   detecting the components that are separated based on their drift times.

2. The spectrometer method of claim 1, wherein applying the cross drift flow to different segments and/or regions of the drift tube.

3. The spectrometer method of claim 1, further comprises adding at least one chemical modifier to the cross drift flow.

4. The spectrometer method of claim 3, wherein applying one chemical modifier to a specific segment and/or region of the drift tube by way of the cross drift flow; and applying a second chemical modifier to a specific segment and/or region of the drift tube by way of the cross drift flow.

5. The spectrometer method of claim 1, further comprises removing neutral molecules in the drift tube along with the drift flow.

6. The spectrometer method of claim 1, wherein providing the cross drift flow is combined with a counter or uni-direction flow.

7. The spectrometer method of claim 6, wherein the counter or uni-direction flow is provided in a segment and/or region of the drift tube and the cross drift flow is provided in another segment and/or region of the drift tube.

* * * * *